(12) United States Patent
Huth et al.

(10) Patent No.: US 9,132,106 B2
(45) Date of Patent: Sep. 15, 2015

(54) SYNERGISTIC OPHTHALMIC COMPOSITIONS FOR DISINFECTING CONTACT LENSES

(71) Applicant: Abbott Medical Optics Inc., Santa Ana, CA (US)

(72) Inventors: Stanley W. Huth, Newport Beach, CA (US); Denise Tran, Irvine, CA (US)

(73) Assignee: ABBOTT MEDICAL OPTICS INC., Santa Ana, CA (US)

(*) Notice: Subject to any disclaimer, the term of this patent is extended or adjusted under 35 U.S.C. 154(b) by 68 days.

(21) Appl. No.: 13/826,257

(22) Filed: Mar. 14, 2013

(65) Prior Publication Data

US 2014/0275274 A1    Sep. 18, 2014

(51) Int. Cl.
*A61K 31/155* (2006.01)
*A01N 37/52* (2006.01)
*A61L 12/14* (2006.01)

(52) U.S. Cl.
CPC .............. *A61K 31/155* (2013.01); *A01N 37/52* (2013.01); *A61L 12/14* (2013.01); *A61L 12/141* (2013.01); *A61L 12/145* (2013.01)

(58) Field of Classification Search
None
See application file for complete search history.

(56) References Cited

U.S. PATENT DOCUMENTS

| | | |
|---|---|---|
| 2002/0122831 A1 | 9/2002 | Mowrey-McKee et al. |
| 2003/0068250 A1 | 4/2003 | Huth et al. |
| 2004/0191284 A1 | 9/2004 | Yu et al. |
| 2006/0047006 A1 | 3/2006 | Salamone et al. |
| 2008/0161266 A1 | 7/2008 | Jani et al. |
| 2010/0104528 A1* | 4/2010 | Marlowe et al. ........... 424/78.08 |
| 2012/0205255 A1* | 8/2012 | Roster et al. ................. 205/626 |
| 2012/0288470 A1 | 11/2012 | Huth et al. |

FOREIGN PATENT DOCUMENTS

WO    WO-9811875 A1    3/1998

OTHER PUBLICATIONS

International Search Report and Written Opinion for Application No. PCT/US2014/018602 mailed on May 26, 2014, 11 pages.

* cited by examiner

*Primary Examiner* — Ernst V Arnold
*Assistant Examiner* — Jianfeng Song

(57) ABSTRACT

Compositions and methods for disinfecting contact lenses using the compositions are disclosed. The compositions include a combination of alexidine and chlorhexidine, which surprisingly causes the composition to exhibit synergistic antimicrobial activity against *Candida albicans* by reducing a concentration of *Candida albicans* by at least 1.2 log.

19 Claims, 2 Drawing Sheets

ND YNERGISTIC OPHTHALMIC
COMPOSITIONS FOR DISINFECTING
CONTACT LENSES

FIELD OF THE INVENTION

The present invention relates in general to contact lens care and, more particularly, to ophthalmic compositions and methods for using the ophthalmic compositions in contact lens care.

BACKGROUND OF THE INVENTION

Contact lenses are disposed in direct contact with and over the cornea of an eye to correct a patient's vision. In many cases, the patient wears the contact lens for several hours or days and then removes the lens for cleaning, storage, and reuse. The lens is placed into a well formed in a lens case, and the well is filled with a multipurpose solution formulated to include various additives, such as an antimicrobial, disinfectant, and/or preservative for reducing the microbial load that has built up on the lens. After cleaning, the lens is removed from the well and directly inserted into the eye.

As is typically the case, many different types of microorganisms can be found on a contact lens and/or in a contact lens case after use. One of the most disinfectant-resistant microorganisms, Candida albicans ("C. albicans"), is a diploid fungus that serves as a pathogen producing colonies of yeast on a surface. The colonies form a biofilm on the contact lens which without cleansing and disinfecting may lead to infection or diseased conditions of the eye. Other microorganisms, such as gram negative bacteria, may be present after wear and may increase the incidence of inflammatory cells or infiltrates invading the cornea. Infiltrates can result in discomfort and intolerance to contact lens wear.

To reduce and/or prevent the likelihood of infection, the multipurpose solution is formulated to be sufficiently strong to be capable of killing unwanted microorganisms, including C. albicans. Additionally, various other factors are considered during formulation of the multipurpose solution. For example, an ideal solution preferably also is compatible with a variety of different contact lens materials, such as silicone hydrogel and the like. Contact lens compatibility can be measured by contact lens discoloration, physical parameter change, fragility, and uptake/release of solution components, such as antimicrobial components. Moreover, the lens solution is preferably further formulated such that ocular surface cell changes, irritation or user discomfort is minimized during use.

Balancing the aforementioned factors continues to be a challenge when formulating the multipurpose solution. In particular, the addition of more disinfecting agents increases a solution's efficacy, but too large an increase in disinfecting agent concentration usually reduces contact lens material compatibility and/or ocular comfort or produces adverse changes in corneal epithelial ocular surface cells, such as cell death commonly known as corneal epithelial punctate fluorescein staining Formulating a solution with less disinfecting agent in turn results in a solution with lower antimicrobial efficacy. Furthermore, disinfecting agents are known to be absorbed into contact lenses themselves, further decreasing a solution's efficacy. Although increasing the concentration of disinfecting agent alleviates the absorption issue, too much disinfecting agent can cause eye irritation, increased corneal epithelial staining and/or presence of infiltrates.

Accordingly, there is a need for a contact lens multipurpose solution that not only provides a desired amount of biocidal efficacy against resistant microorganisms, such as C. albicans and other endotoxic bacteria, but does so with minimized ocular discomfort to the patient. Additionally, there is a need for a multipurpose solution that maintains a sufficiently high disinfectant potential while reducing an incidence of infiltrates and/or corneal staining.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DEFINITION OF TERMS

Figure 1:
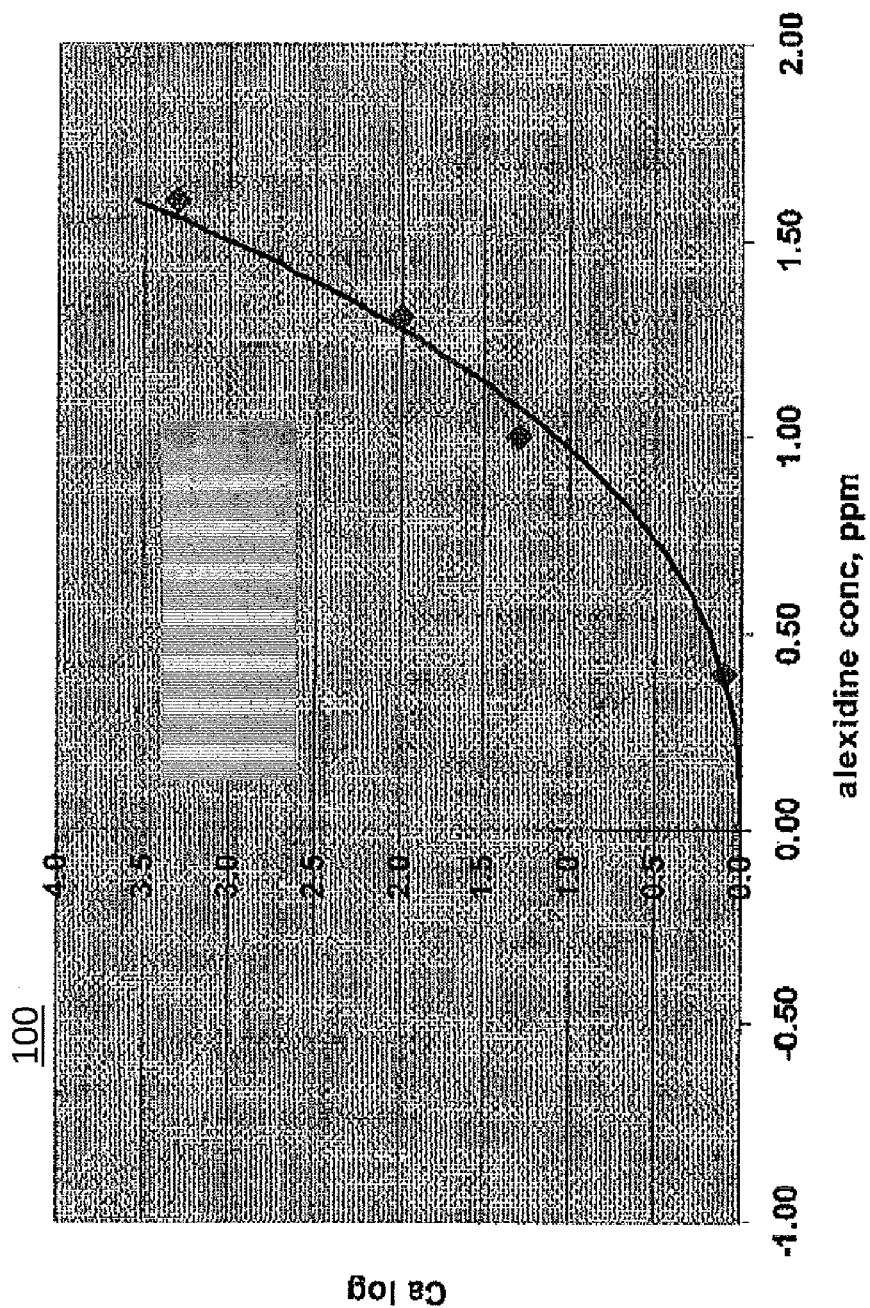
FIG. 1 is a graph showing antimicrobial activity of alexidine against Candida albicans as a concentration of alexidine increases.

Antimicrobial: As used herein, the term "antimicrobial" refers to any agent or action that results in biocidal, antimicrobial, antibacterial, or antifungal activity against any microbe. A skilled artisan will appreciate that antimicrobial as used herein also refers to a disinfectant or preservative (e.g., of an ocular solution).

Ophthalmic: As used herein, the term "ophthalmic" or ophthalmic composition/solution refers to anything associated with the eyes, including compositions to treat ocular conditions (e.g., dry eye, infection or inflammation) and contact lens compositions (e.g., re-wetters, disinfecting solutions, storage solutions, cleaning solutions, rinsing solutions, and multi-purpose solutions). Of course, multi-purpose contact lens care solutions are those that may be used to re-wet, disinfect, clean, store, and rinse contact lenses. The ophthalmic compositions containing antimicrobial components disclosed herein allow a user to remove a contact lens exposed to the composition and place the lens directly in the user's eye for safe and comfortable wear or, after the lens is exposed to the ophthalmic composition, it may be rinsed with another quantity of the ophthalmic composition and placed in the user's eye for safe and comfortable wear.

Ophthalmically Acceptable: As used herein, the terms "ophthalmically acceptable" refers to a contact lens care solution or component thereof that is compatible with ocular tissue, i.e., it does not cause significant or undue detrimental effects when brought into contact with ocular tissue.

Synergistically-effective: As used herein, the term "synergistically-effective" and "synergistically-antimicrobial" refer to any combined amount antimicrobial compound or compounds that exhibit synergistic biocidal, antimicrobial, antibacterial, or antifungal activity against at least one microbe. As used herein, "synergistic" and "synergistically" refer to the effect achieved with a combination of components when that effect is greater than the sum of the effects achieved with either component alone.

DETAILED DESCRIPTION OF THE INVENTION

Ophthalmic compositions and methods of disinfecting a contact lens using the composition are provided. The ophthalmic compositions include antimicrobial components, in particular, alexidine and chlorhexidine, at relatively low concentrations that when combined surprisingly exhibit antimicrobial activity that is above and beyond the sum of antimicrobial activity of either alexidine or chlorhexidine alone at the same low concentrations. This unexpected synergistic effect is exhibited when a microorganism, such as *Candida albicans*, is contacted with a solution including the ophthalmic composition. After a period of time, a concentration of *C. albicans* is reduced by at least 1.2 log.

Generally, the ophthalmic compositions comprise a combination of alexidine and chlorhexidine, the combination being present in an amount effective to disinfect a contact lens contacted with the composition. The composition may be included in a liquid aqueous medium forming a solution and may further include other components which are typically found in multi-purpose lens care solutions.

In an embodiment, the other components in the composition include one or more additional antimicrobial agents other than alexidine and chlorhexidine, in an amount effective in enhancing antimicrobial activity of the composition. The additional antimicrobial components are chemicals which derive their antimicrobial activity through a chemical or physiochemical interaction with microbes or microorganisms, such as those microbes or microorganisms contaminating a contact lens. As such, in an embodiment of the present invention, the ophthalmic composition includes the combination of alexidine and chlorhexidine and one or more of the additional antimicrobial agents.

In another embodiment, the other components in the composition include a chelating or sequestering agent and/or a surfactant component, the chelating agent in an amount effective for solution preservation and the surfactant component in an amount effective in cleaning a contact lens contacted with the composition. For example, the composition including the combination of alexidine and chlorhexidine includes the surfactant component and optionally, the additional antimicrobial agent. In an alternate example, the composition includes the combination of alexidine and chlorhexidine includes the surfactant component and an additional antimicrobial agent. In an alternative example, the composition including the combination of alexidine and chlorhexidine includes the chelating or sequestering agent, and optionally includes the additional antimicrobial agent and/or the surfactant. An alternate example may be a composition comprising a combination of alexidine and chlorhexidine, a chelating or sequestering agent, an additional antimicrobial agent and a surfactant. A further example may have a composition comprising a combination of alexidine and chlorhexidine, a chelating or sequestering agent and a surfactant.

In another embodiment, the composition including the combination of alexidine and chlorhexidine includes a buffering agent in an amount effective in maintaining the pH of the composition within a physiologically acceptable range.

An alternate example may be a composition comprising a combination of alexidine and chlorhexidine, a chelating or sequestering agent, a surfactant and a tonicity component.

A further alternate example may be a composition comprising a combination of alexidine and chlorhexidine, a chelating or sequestering agent, an additional antimicrobial agent, a surfactant and a tonicity component.

In still another embodiment of the present invention, the composition including the combination of alexidine and chlorhexidine additionally includes effective amounts of one or both of a viscosity-inducing component and a tonicity component. Such an embodiment optionally includes one or more of the additional antimicrobial agent, chelating or sequestering agent, the surfactant component, and/or the buffer agent.

Each of the components, in the concentration employed, included in the solutions of the present invention preferably are ophthalmically acceptable. In addition, each of the components, in the concentration employed, included in the present solutions are soluble in a liquid aqueous medium. Moreover, the compositions are substantially ophthalmically optimized such that, within the constraints of component chemistry, the compositions minimize ocular response.

As noted briefly above, the composition includes a combination of alexidine and chlorhexidine at relatively low concentrations. The composition includes a total concentration of alexidine and chlorhexidine in a range of about 1.5 ppm to about 6.6 ppm, preferably in a range of about 1.7 ppm to about 6.3 ppm, and more preferably in a range of about 2.2 ppm to about 3.90 ppm. In another embodiment, the composition includes about 0.70 ppm to about 1.3 ppm alexidine and about 1.00 ppm to about 5.00 ppm chlorhexidine. In still another embodiment, the composition includes about 0.70 ppm to about 1.15 ppm alexidine and about 1.5 ppm to about 2.75 ppm chlorhexidine. In yet another embodiment, the composition includes about 0.50 ppm to about 1.15 ppm alexidine and about 1.0 ppm to about 5.5 ppm chlorhexidine. Various forms of alexidine and chlorhexidine, for example, salts of alexidine, alexidine-free base, and/or salts of chlorhexidine may be included in the compositions.

The dihydrochloride salt of alexidine, alexidine 2 HCl, was used in the examples discussed herein. One of ordinary skill in the art will appreciate that an equivalent amount of another form of alexidine can alternatively or additionally be used, expressed preferably in functional properties or in molecular equivalents of alexidine. For the purposes of the present invention "alexidine" will be used to refer to any and all such forms of alexidine.

The digluconate salt of chlorhexidine was used in the examples discussed herein. Similarly, one of ordinary skill in the art will appreciate that an equivalent amount of another form of chlorhexidine can alternatively or additionally be used, also expressed preferably in functional properties or in molecular equivalents of chlorhexidine. For the purposes of the present invention "chlorhexidine" will be used to refer to any and all such forms of chlorhexidine.

The additional antimicrobial components that, optionally, are generally employed in the ophthalmic composition include, but are not limited to: quaternary ammonium salts used in ophthalmic applications such as benzalkonium halides, and biguanides, such as hexamethylene biguanides, polyhexamethylene biguanides, and salts thereof, antimicrobial polypeptides, and the like and mixtures thereof. For example, a polyquaternary ammonium compound poly[(dimethyliminio)-2-butene-1,4-diyl chloride], α-[4-[tris(2-hydroxyethyl) ammonio]-2-butenyl]-Ω-[tris(2-hydroxyethyl) ammonio]-dichloride, known as Polyquaternium-1 (Onyx Corporation, Jersey City, N.J.) or any additional antimicrobial components are present in the liquid aqueous medium at an ophthalmically acceptable or safe concentration such that the user can remove the disinfected lens from the liquid aqueous medium and immediately thereafter directly place the lens in the eye for safe and comfortable wear, with minimal, if any, incidence of corneal epithelial punctate fluorescein staining.

In an embodiment of the present invention, the present composition optionally incorporates the Polyquaternium-1 in a range of about 0.50 ppm to about 5.00 ppm, preferably in the range of about 1.50 ppm to about 3.30 ppm, and more preferably in a range of about 1.0 ppm to about 3.3 ppm.

The chelating component or chelating agent preferably is included in an amount that enhances the efficacy of the antimicrobial component and/or complexes with any metal ions to more effectively clean the contact lens. A wide range of organic acids, amines, or compounds which include an acid group and an amine function, are capable of acting as chelating components in the present compositions. For example, nitrilotriacetic acid, diethylenetriaminepentacetic acid, hydroxyethylethylene-diaminetriacetic acid, 1,2-diaminocyclohexane tetraacetic acid, hydroxyethylaminodiacetic acid, ethylenediaminetetraacetic acid and its salts and polyphosphates are useful as chelating components. Ethylenediaminetetraacetic acid (EDTA) and its alkali metal salts, are preferred, with disodium salt of EDTA, also known as disodium edetate, being particularly preferred.

The chelating component preferably is present in an effective amount, for example, in a range of about 0.04% to about 1.0% (w/v) of the solution or preferably, in a range of about 0.05% to about 1.0% (w/v). In a very useful embodiment, particularly when the chelating component is EDTA, salts thereof and mixtures thereof, an amount of the chelating component in a range of about 0.04% to about 0.15% (w/v) is preferably employed, and more preferably an amount in the range of about 0.05% to about 0.15% (w/v) of the solution. Such amounts of chelating component have been found to be effective in the present compositions while, at the same time, providing for reduced discomfort and/or ocular irritation.

The surfactant may be added to the disclosed compositions to aid in cleaning, e.g., to at least aid in removing debris or deposit material from a contact lens contacted with the solution. Some exemplary surfactant(s) include, but are not limited to, nonionic surfactants, e.g., 4-(1,1,3,3-tetramethylbutyl) phenol/poly(oxyethylene) polymers (e.g. Tyloxapol® also obtained from Sigma-Aldrich Co.), poly(oxyethylene)-poly(oxypropylene) block copolymers, and combinations of these and/or other surfactants.

Nonionic surfactants may be used in some embodiments of compositions disclosed herein. Nonionic surfactants include poly(oxyethylene)-poly(oxypropylene) block copolymers (poloxamers), which may be obtained commercially from the BASF Corporation of Florham Park, N.J. under the trademarks Pluronic® or Tetronic®. Pluronic® block copolymers generally can be described as polyoxyethylene/polyoxypropylene condensation polymers terminated in primary hydroxyl groups. Pluronic® block copolymers may be synthesized by first creating a hydrophobe of desired molecular weight by the controlled addition of propylene oxide to the two hydroxyl groups of propylene glycol or glycerin. An ethylene oxide then may be added to sandwich the hydrophobe between hydrophile groups. Tetronic® surfactants are known as poloxamines and are symmetrical block copolymers of ethylene diamine with polyoxyethylene and polyoxypropylene.

In some embodiments, the block copolymers have average molecular weights in the range of about 2500 to about 30,000 Daltons, more preferably, about 6000 to about 18,000 Daltons. Exemplary block copolymer surfactants include: poloxamer 108, poloxamer 188, poloxamer 237, poloxamer 238, poloxamer 288 poloxamer 407, Pluronic® F68, Pluronic® F87, Pluronic® F127, Pluronic® P103, Tetronic® 304, Tetronic® 904, Tetronic® 1107, Tetronic® 1304 (mol. wt. 10,500), and Tetronic® 1307.

The amount of surfactant present, if any, varies over a wide range depending on a number of factors, including, the particular surfactant(s) used, any other components in the composition, and the like. The amount of surfactant included in the composition is in a range of about 0.03% to about 1.00% (w/v) or in a range of about 0.03% to about 0.15% (w/v).

If the disclosed compositions will directly contact the eyes, it is preferred that the compositions have a pH in the physiologically acceptable range of about 6 to about 8. In particular, the solution preferably has a pH in the range of about 7 to about 8. In order to achieve or maintain the desired pH, a buffer component or buffer agent in an amount effective to maintain the pH may be required. The buffer component may include boric acid and/or sodium borate (e.g., sodium borate 10 hydrate), which have been found to enhance a disinfecting effect of a composition. Citric acid and its salts (e.g., trisodium citrate), tartaric acid and its salts, other organic acids and the like and mixtures thereof may be used as a buffer. Alternatively, the buffer component may include one or more phosphate or tromethamine (TRIS, 2-amino-2-hydroxymethyl-1,3-propanediol) buffers, for example, combinations of monobasic phosphates, dibasic phosphates, and the like, or tromethamine and tromethamine hydrochloride. Particularly useful phosphate buffers are those selected from phosphate salts of alkali metals. Examples of suitable phosphate buffers include one or more of sodium phosphate dibasic ($Na_2HPO_4$), sodium phosphate monobasic ($NaH_2PO_4$), and the corresponding potassium phosphate salts. Other examples of the buffer component may include an amino acid such as taurine. Buffer components typically are used in amounts from about 0.01% to about 1.0% (w/v). In an embodiment, the composition includes boric acid in a range of about 0.50% to about 0.66% (w/v) and sodium borate in a range of about 0.15% to about 0.25% (w/v).

The viscosity-inducing components employable in the present compositions preferably are those that are effective at low or reduced concentrations, are compatible with other components of the present compositions, and are nonionic. Such viscosity-inducing components may act to enhance and/or prolong the cleaning and wetting activity of any surfactant component, condition the lens surface making it more hydrophilic/less lipophilic, and/or to act as a demulcent in the eye. Increasing solution viscosity also may provide a film on the lens to facilitate comfortable wear. The viscosity-inducing component also may act to cushion the impact of contact lens insertion on the surface of the eye and may serve to alleviate eye irritation.

Suitable viscosity-inducing components include, but are not limited to, sodium hyaluronate, water soluble natural gums, cellulose-derived polymers and the like. Natural gums include guar gum, gum tragacanth, and the like. Cellulose-derived polymers include hydroxypropyl cellulose, hydroxypropylmethyl cellulose, methyl cellulose, hydroxyethyl cellulose, and the like. Preferred viscosity-inducing agents include cellulose derivatives (polymers), and mixtures thereof. A particularly useful viscosity-inducing component is hydroxypropylmethyl cellulose (HPMC).

The viscosity-inducing component is used in an amount effective to increase the viscosity of the solution, preferably to a viscosity in the range of about 1.3 to about 30 cps, or even as high as about 75 cps (measured at 25° C.), preferably as determined by The United States Pharmacopeial Convention (USP) Test Method No. 911 (USP 23, 1995). To achieve this range of viscosity increase, about 0.05% to about 0.25% (w/v), or about 0.04% to about 0.15% (w/v), of a viscosity-inducing component, such as HPMC, is employed.

The liquid aqueous medium used in conjunction with the present compositions is selected to have no substantial deleterious effect on the lens being treated, or on the wearer of the treated lens. The liquid medium is constituted to permit, and even facilitate, the lens treatment or treatments by the present compositions. The liquid aqueous medium advantageously has an osmolality in the range of at least about 200-mOsmol/kg for example, about 300 or about 350, to about 400 mOsmol/kg. The liquid aqueous medium more preferably is substantially isotonic or hypotonic (for example, 250 mOsmol/kg hypotonic) and/or is ophthalmically acceptable.

The liquid aqueous medium preferably includes an effective amount of a tonicity component to provide the liquid medium with the desired tonicity. Such tonicity components may be present in the liquid aqueous medium and/or may be introduced into the liquid aqueous medium. Among the suitable tonicity adjusting components that may be employed are those conventionally used in contact lens care products, such as various inorganic salts and non-ionic polyols. Sodium chloride (NaCl) and/or potassium chloride (KCl) and the like are very useful tonicity components, as are propylene glycol, glycerin, sorbitol, mannitol and the like. The amount of tonicity component included is effective to provide the desired degree of tonicity to the solution. Such amount may be, for example, in the range of about 0.10% to about 0.8% (w/v). For example, sodium chloride is included in a range of about 0.18% to about 0.70% (w/v). If a combination of sodium chloride and potassium chloride is employed, it is preferred that the weight ratio of sodium chloride to potassium chloride be in the range of about 3 to about 6 or about 8.

Methods for disinfecting a contact lens using the composition described herein are included within the scope of the invention. Such methods comprise contacting a contact lens with the composition at conditions effective to provide the desired treatment to the contact lens. Contacting parameters include, among others, temperature, pressure and time. Contacting temperature may be in the range of about 0° C. to about 100° C., more preferably in the range of about 10° C. to about 60° C., and still more preferably in the range of about 15° C. to about 30° C. Contacting at about ambient temperature is typical. The contacting may occur at about atmospheric pressure. The contacting preferably occurs for a time in a range of about 5 minutes or about 1 hour to about 2 hours, about 4 hours, about 6 hours, or about 12 hours or more. As described herein, such a composition may include other ingredients including, but not limited to, a viscosity enhancing agent to, for example, increase the residence time of the composition in the eye or to increase user comfort.

A contact lens can be contacted with a liquid aqueous medium including the composition in association with the method of the present invention by immersing the lens in the medium. During at least a portion of the contacting, the liquid medium containing the contact lens can be agitated, for example, by shaking the container containing the liquid aqueous medium and contact lens, to at least facilitate removal of deposit material from the lens. After such contacting step, the contact lens may be manually rubbed to remove further deposit material from the lens. The cleaning method can also include rinsing the lens with the liquid aqueous medium prior to returning the lens to a wearer's eye. In one embodiment, the lens can be substantially free of the liquid aqueous medium prior to returning the lens to a wearer's eye. However, the method may also be as simple as removing the lens from the lens case, and placing the lens directly in an eye either with or without removing the liquid aqueous medium prior to placing the lens in the wearer's eye.

As will be shown in the examples below, the presence of *C. albicans* is reduced by at least 1.2 log, after the lens has been exposed to the compositions described above including the combination of relatively low concentrations of alexidine and chlorhexidine. When the lens is exposed to compositions using only alexidine or chlorhexidine, higher concentrations of each are needed in order to produce an acceptable log kill of *C. albicans*.

The following examples are presented to illustrate aspects and features of various embodiments of the present inventive subject matter, and are not to be taken as limiting the inventive subject matter in any respect.

Example 1

The test procedure for testing antimicrobial activity against specified test organisms is as follows: A 10-mL aliquot of test sample was transferred into a single polypropylene test tube. Sterile Dulbecco's Phosphate-Buffered Saline with 0.05 w/v % Polysorbate 80 (DPBST) was transferred into a separate polypropylene test tube and used as a control. All samples and control were stored at 20-25° C. throughout the duration of the test. Test cultures of specified test organisms were cultured and prepared in the conventional manner using Saboraud Dextrose Agar (SDA) as the growth medium. The challenge organism inoculum was adjusted to approximately $1 \times 10e7$-$1 \times 10e8$ CFU/mL in DPBST. Fifty µL of culture inoculum was added to 10.0 mL of each test sample and control, so that the final inoculum level was in the range of $1 \times 10e5$ to $1 \times 10e6$ CFU (colony forming units) per mL of specified test organism. Contact time intervals for testing activity against the specified test organism were typically within 4 or 6 hours, e.g., 15 minutes, 30 minutes, 45 minutes, 1 hour, 2 hours, 4 hours and 6 hours, to remain within the intended product label instructions for maximum contact lens soak time.

Following incubation, the number of surviving organisms was enumerated by serial dilution and culture on SDA medium. An appropriate neutralizing disinfectant medium was used for performing serial dilutions (e.g. Letheen Neutralizing Broth containing 0.5% Polysorbate 80 media—LetheenT80). Additionally, the numbers of colony-forming-units (CFU) were counted and the Log 10 reduction in viable number calculated for test solutions based on the initial time zero challenge inoculum in the control solution.

The example ophthalmic solutions 1-3 were prepared with the components and amounts listed in Table 1. The Polyquaternium-1 used in this and all examples was a high-molecular weight (Hmw) Polyquaternium-1 as described in U.S. Pat. No. 7,795,374, incorporated herein in its entirety. The components were added to purified water at room temperature (e.g., about 25° C.) with gentle stirring.

TABLE 1

| Components | Solution 1 | Solution 2 | Solution 3 |
|---|---|---|---|
| Alexidine 2HCl, ppm | 1.60 | 1.30 | 1.00 |
| Hmw Polyquaternium-1, ppm | 3.01 | 3.01 | 3.01 |
| EDTA | 0.05 | 0.05 | 0.05 |
| NaCl | 0.25 | 0.25 | 0.25 |
| Boric Acid | 0.60 | 0.60 | 0.60 |
| Sodium Borate 10H2O | 0.15 | 0.15 | 0.15 |
| Trisodium Citrate 2H2O | 0.65 | 0.65 | 0.65 |
| Tetronic ® 904 | 0.10 | 0.10 | 0.10 |

Log kill activity measurements of *C. albicans* were taken after 6 hours of soaking in solutions 1-3. An additional formula included only 0.4 ppm alexidine along with the other components in solutions 1-3 in identical amounts. This latter solution produced a 6-hour log kill of *C. albicans* of 0.1.

FIG. 1 is a graph 100 plotting measured and extrapolated results. In particular, graph 100 includes an x-axis including alexidine concentrations for each of the solutions 1-3 in Table I and the fourth solution with 0.4 ppm alexidine and a y-axis including the log kill measurements of *C. albicans* taken after the 6 hour soaking step. As shown in graph 100, alexidine at 1.00 ppm achieves a 1.3 log kill, which is not sufficient activity to consistently meet the contact lens multi-purpose disinfection solution stand-alone activity standard for *C. albicans* of 1.0 log kill, given the test method variation for *C. albicans* kill and the need to meet this standard at the end of the product shelf life, where the disinfecting agent(s) may have degraded by about 20% or about 20% have been lost to container adsorption. In other words, a 1.0 log kill is acceptable at the end of product shelf life, but not at the beginning. Although alexidine at 1.3 ppm and 1.6 ppm provide the stand-alone activity standard for *C. albicans*, inclusion of such amounts of alexidine has been found to increase corneal staining potential. The inclusion of Polyquaternium-1 (PQ-1) in solutions 1-3 and the fourth solution does not affect the amount of alexidine needed to achieve the log kill of *C. albicans*, as PQ-1 has little effect on *C. albicans* in the presence of 0.65% trisodium citrate dihydrate.

For the second part of this example, the ophthalmic solutions 4-8 were prepared with the components and amounts listed in Table 2. The components were added to purified water at room temperature (e.g., about 25° C.) with gentle stirring.

TABLE II

| Components | Solution 4 | Solution 5 | Solution 6 | Solution 7 | Solution 8 |
|---|---|---|---|---|---|
| Chlorhexidine digluconate, ppm | 5.00 | 10.02 | 15.02 | 20.01 | 25.00 |
| Hmw Polyquaternium-1, ppm | 3.00 | 3.00 | 3.00 | 3.00 | 3.00 |
| EDTA | 0.05 | 0.05 | 0.05 | 0.05 | 0.05 |
| NaCl | 0.25 | 0.25 | 0.25 | 0.25 | 0.25 |
| Boric Acid | 0.60 | 0.60 | 0.60 | 0.60 | 0.60 |
| Sodium Borate 10H2O | 0.15 | 0.15 | 0.15 | 0.15 | 0.15 |
| Trisodium Citrate 2H2O | 0.65 | 0.65 | 0.65 | 0.65 | 0.65 |
| Tetronic ® 904 | 0.10 | 0.10 | 0.10 | 0.10 | 0.10 |

Figure 2:
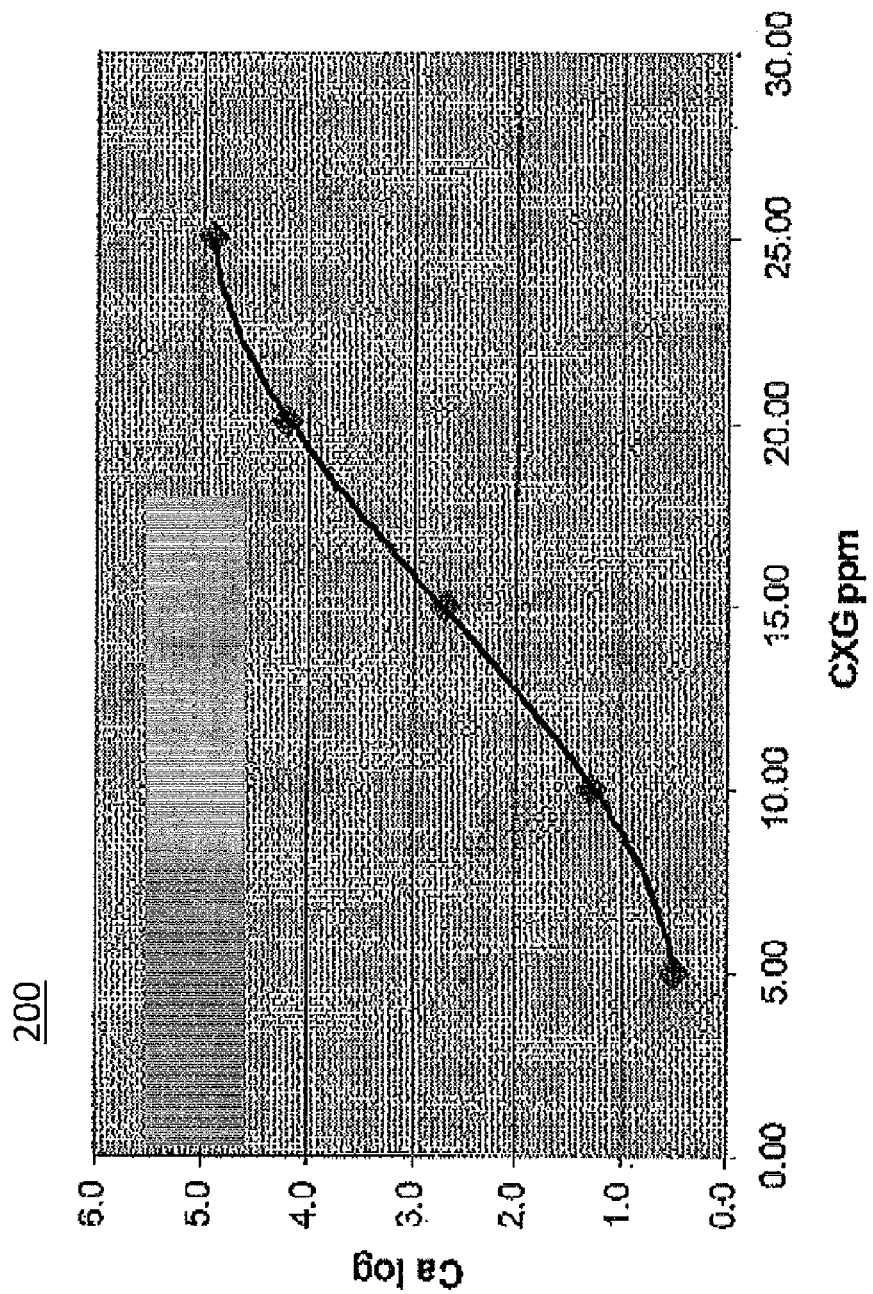
FIG. 2 is a graph showing antimicrobial activity of chlorhexidine against Candida albicans as a concentration of chlorhexidine increases.

Measurements of log kill activity of *C. albicans* were taken after 6 hours of soaking in the solutions 4-8. FIG. 2 is a graph 200 showing the plotted measured results. In particular, graph 200 includes an x-axis including chlorhexidine concentrations for each of the solutions 4-8 in Table II and a y-axis including the log kill measurements of *C. albicans* taken after the 6 hour soaking step. As shown in FIG. 2, in order for a composition to achieve a 2-log or 3-log kill against *C. albicans*, chlorhexidine needs to be included in an excess of 12 ppm and 15 ppm, respectively. These amounts of chlorhexidine may produce undesirable effects, such as increased corneal staining. The inclusion of Polyquaternium-1 (PQ-1) in solutions 4-8 does not affect the amount of chlorhexidine needed to achieve a desired log kill of *C. albicans*, as PQ-1 has little effect on *C. albicans* in the presence of 0.65% trisodium citrate dihydrate.

In the third part of this example, solutions shown in Table III below were prepared and tested according to the methods described above. The solutions in Table III include one solution with 1.05 ppm alexidine and no chlorhexidine (82-3), one solution with 5.00 ppm chlorhexidine and no alexidine (82-2) and one solution representing compositions of the present invention with both alexidine and chlorhexidine (82-1), at the same concentrations respectively as the other solutions. A fourth solution (82-4), containing a higher concentration of alexidine and no chlorhexidine, is included for comparison. These solutions were tested against the complete FDA panel of microorganisms required for contact lens multi-purpose disinfecting solutions, with the addition of *Acanthamoeba*. It can be seen in Table III that solution 82-1 exhibits dramatic synergistic activity against *C. albicans* and passes all other FDA "stand-alone" criteria for contact lens multi-purpose solutions. That is, the *C. albicans* log kill of solution 82-1 of 3.1 logs, far exceeds the 1.7 log kill sum of log kills for solutions 82-2 (0.2 log) and 82-3 (1.5 log). Herein, we define the synergy ratio as the log kill synergy result divided by the sum of log kills of the alexidine alone and chlorhexidine alone=3.1/1.7=1.82. The FDA "stand-alone" criteria for contact lens multi-purpose solutions includes at least a 3.0 log kill for each of the bacteria (*Staph aureus*, *Pseudomonas aeruginosa* and *Serratia marcescens*) and at least a 1.0 log kill for *C. albicans* and *F. solani*.

TABLE III

| Ingredients | DT1200-82-1 | DT1200-82-2 | DT1200-82-3 | DT1200-82-4 |
|---|---|---|---|---|
| Alexidine 2HCl, ppm | 1.05 | 0 | 1.05 | 1.60 |
| Chlorhexidine digluconate, ppm | 5.01 | 5.00 | 0 | 0 |
| Hmw PQ-1, ppm | 3.00 | 3.01 | 3.00 | 3.00 |
| EDTA | 0.05 | 0.05 | 0.05 | 0.05 |
| NaCl | 0.25 | 0.25 | 0.25 | 0.25 |
| Boric acid | 0.60 | 0.60 | 0.60 | 0.60 |
| Sodium borate 10H20 | 0.15 | 0.15 | 0.15 | 0.15 |
| Trisodium citrate 2H20 | 0.65 | 0.65 | 0.65 | 0.65 |
| Tetronic 904 | 0.10 | 0.10 | 0.10 | 0.10 |
| *Staph aureus* ATCC 6538 6 hr log kill | 4.7 | 3.7 | 4.7 | 4.7 |
| *Pseudomonas aeruginosa* ATCC 9027 6 hr log kill | 4.7 | 4.7 | 4.7 | 4.7 |
| *Serratia marcescens* ATCC 13880 6 hr log kill | 4.6 | 3.5 | 4.6 | 4.6 |
| *Candida albicans* ATCC 10231 6 hr log kill | 3.1 | 0.2 | 1.5 | 2.7 |
| *Fusarium solani* ATCC 36031 6 hr log kill | 4.6 | 4.6 | 4.6 | 4.6 |
| *Acanthamoeba castellanii trophs* ATCC 50370 6 h | 3.9 | 2.7 | 3.4 | 3.4 |

Example 2

In this example, solutions shown in Tables IV and V below were prepared and tested according to the methods described above. In this example, Pluronic F87 surfactant at 0.05% replaced the Tetronic 904 surfactant in Example 1. This example also included 0.039% of a viscosity polymer, HPMC.

lens case of a patient with a corneal infiltrate, but the enhanced kill against this organism exhibited by the alexidine-chlorhexidine system (2.7, 4.1 and 4.6 log) vs the alexidine-only control at 1.60 ppm alexidine (2.3 log) is a significant positive attribute, as Achromobacter species are believed to contribute to the production of corneal infiltrates.

TABLE IV

| Ingredients | DT1110-13-1 | DT1110-13-2 | DT1110-13-3 | DT1110-13-4 |
|---|---|---|---|---|
| Alexidine 2HCl, ppm | 1.05 | 0 | 1.05 | 0 |
| Chlorhexidine digluconate (CXG), ppm | 1.00 | 1.00 | 2.00 | 2.00 |
| Hmw PQ-1, ppm | 3.00 | 3.00 | 3.00 | 3.01 |
| EDTA | 0.10 | 0.10 | 0.10 | 0.10 |
| NaCl | 0.22 | 0.22 | 0.22 | 0.22 |
| Boric acid | 0.60 | 0.60 | 0.60 | 0.60 |
| Sodium borate 10H20 | 0.182 | 0.182 | 0.182 | 0.182 |
| Trisodium citrate 2H20 | 0.65 | 0.65 | 0.65 | 0.65 |
| Tetronic 904 | 0 | 0 | 0 | 0 |
| Pluronic F87 | 0.05 | 0.05 | 0.05 | 0.05 |
| HPMC | 0.0390 | 0.0391 | 0.0390 | 0.0390 |
| *Candida albicans* ATCC10231 6 hr log kill | 2.6 | 0.2 | 2.8 | 0.3 |
| sum, alex only + CXG only | 1.8 | | 1.9 | |
| *Candida* log kill synergy ratio | 1.44 | | 1.47 | |
| *Achromobacter* sp. AH-2C 6 hr log kill | 2.7 | 2.3 | 4.1 | 3.1 |
| sum, alex only + CXG only | 4.7 | | 5.5 | |

TABLE V

| Ingredients | DT1110-13-5 | DT1110-13-6 | DT1110-13-7 | DT1110-13-8 |
|---|---|---|---|---|
| Alexidine 2HCl, ppm | 1.05 | 0 | 1.05 | 1.60 |
| Chlorhexidine digluconate (CXG), ppm | 3.00 | 3.00 | 0 | 0 |
| Hmw PQ-1, ppm | 3.00 | 3.00 | 3.01 | 3.01 |
| EDTA | 0.10 | 0.10 | 0.10 | 0.05 |
| NaCl | 0.22 | 0.22 | 0.22 | 0.25 |
| Boric acid | 0.60 | 0.60 | 0.60 | 0.60 |
| sodium borate 10H20 | 0.182 | 0.182 | 0.182 | 0.15 |
| Trisodium citrate 2H20 | 0.65 | 0.65 | 0.65 | 0.65 |
| Tetronic 904 | 0 | 0 | 0 | 0.10 |
| Pluronic F87 | 0.05 | 0.05 | 0.05 | 0 |
| HPMC | 0.0390 | 0.0390 | 0.0390 | 0 |
| *Candida albicans* ATCC10231 6 hr log kill | 2.9 | 0.3 | 1.6 | 3.7 |
| sum, alex only + CXG only | 1.9 | | | |
| *Candida* log kill synergy ratio | 1.53 | | | |
| *Achromobacter* sp. AH-2C 6 hr log kill | 4.6 | 3.4 | 2.4 | 2.3 |
| sum, alex only + CXG only | 5.8 | | | |

The results again demonstrate synergistic activity against *C. albicans* for solutions 13-1, 13-3 and 13-5, representing compositions of the present invention. Synergy was observed independently for 1.00, 2.00 and 3.00 ppm chlorhexidine, all in combination separately with 1.05 ppm alexidine. No synergy is seen with Achromobacter AH-2C, isolated from the

Example 3

In this example, solutions shown in Table VI below were prepared and tested according to the methods described above. In this example, Pluronic F87 surfactant at 0.10%, along with 0.039% HPMC was used.

TABLE VI

| Ingredients | DT1110-54-1 | DT1110-54-2 | DT1110-54-3 | DT1110-54-4 | DT1110-54-5 |
|---|---|---|---|---|---|
| Alexidine 2HCl, ppm | 1.05 | 1.05 | 0 | 1.05 | 0 |
| Chlorhexidine digluconate (CXG), ppm | 0 | 1.00 | 1.00 | 3.00 | 3.00 |
| Hmw PQ-1, ppm | 3.00 | 3.00 | 3.00 | 3.00 | 3.00 |
| EDTA | 0.10 | 0.10 | 0.10 | 0.10 | 0.10 |
| NaCl | 0.22 | 0.22 | 0.22 | 0.22 | 0.22 |
| Boric acid | 0.60 | 0.60 | 0.60 | 0.60 | 0.60 |
| Sodium borate 10H20 | 0.182 | 0.182 | 0.182 | 0.182 | 0.182 |
| Trisodium citrate 2H20 | 0.65 | 0.65 | 0.65 | 0.65 | 0.65 |
| Pluronic F87 | 0.10 | 0.10 | 0.10 | 0.10 | 0.10 |
| HPMC | 0.039 | 0.039 | 0.039 | 0.039 | 0.039 |

TABLE VI-continued

| Ingredients | DT1110-54-1 | DT1110-54-2 | DT1110-54-3 | DT1110-54-4 | DT1110-54-5 |
|---|---|---|---|---|---|
| *Candida albicans* 10231 6 hr log kill | 1.1 | 1.5 | 0.1 | 3.4 | 0.3 |
| sum, alex only + CXG only | | 1.2 | | 1.4 | |
| synergy ratio | | 1.25 | | 2.43 | |

The results again demonstrate synergistic activity against *C. albicans* for solutions 54-2 and 54-4, representing compositions of the present invention.

Example 4

In this example, solutions shown in Tables VII, VIII and IX below were prepared and tested according to the methods described above.

TABLE VII

| Ingredients | DT1110-44-1 | DT1110-44-2 | DT1110-44-3 | DT1110-44-4 | DT1110-44-5 | DT1110-44-6 |
|---|---|---|---|---|---|---|
| Alexidine 2HCl, ppm | 1.05 | 1.05 | 1.05 | X | X | X |
| Chlorhexidine Digluconate, ppm | X | 1.00 | 3.00 | X | 1.00 | 3.00 |
| Hmw PQ-1, ppm | 3.00 | 3.00 | 3.01 | 3.00 | 3.00 | 3.00 |
| Tetronic 904 | 0 | 0 | 0 | 0 | 0 | 0 |
| EDTA | 0.1 | 0.1 | 0.1 | 0.1 | 0.1 | 0.1 |
| NaCl | 0.22 | 0.22 | 0.22 | 0.22 | 0.22 | 0.22 |
| Boric acid | 0.6 | 0.6 | 0.6 | 0.6 | 0.6 | 0.6 |
| Sodium borate 10H2O | 0.182 | 0.182 | 0.182 | 0.182 | 0.182 | 0.182 |
| Trisodium citrate 2H2O | 0.65 | 0.65 | 0.65 | 0.65 | 0.65 | 0.65 |
| HPMC, % | 0.039 | 0.039 | 0.039 | 0.039 | 0.039 | 0.039 |
| *C. albicans* 10231 6 hr log kill | 1.3 | 3.1 | 2.2 | 0.1 | 0.2 | 0.3 |
| sum, alex only + CXG only | | 1.5 | 1.6 | | | |
| *Candida* log kill synergy ratio | | 2.07 | 1.38 | | | |

TABLE VIII

| Ingredients | DT1110-44-7 | DT1110-44-8 | DT1110-44-9 |
|---|---|---|---|
| Alexidine 2HCl, ppm | 1.05 | 1.05 | X |
| Chlorhexidine Digluconate, ppm | X | 3.00 | 3.00 |
| Hmw PQ-1, ppm | 3.00 | 3.00 | 3.00 |
| Tetronic 904 | 0.05 | 0.05 | 0.05 |
| EDTA | 0.1 | 0.1 | 0.1 |
| NaCl | 0.22 | 0.22 | 0.22 |
| Boric acid | 0.6 | 0.6 | 0.6 |
| Sodium borate 10H2O | 0.182 | 0.182 | 0.182 |
| Trisodium citrate 2H2O | 0.65 | 0.65 | 0.65 |
| HPMC, % | 0.039 | 0.039 | 0.039 |
| *C. albicans* 10231 6 hr log kill | 1.9 | 2.8 | 0 |
| sum, alex only + CXG only | | 1.9 | |
| *Candida* log kill synergy ratio | | 1.47 | |

TABLE IX

| Ingredients | DT1110-44-10 | DT1110-44-11 | DT1110-44-12 | DT1110-44-13 | DT1110-44-14 | DT1110-44-15 |
|---|---|---|---|---|---|---|
| Alexidine, ppm | 1.05 | 1.05 | 1.05 | X | X | X |
| Chlorhexidine, ppm | X | 1.00 | 3.00 | X | 1.00 | 3.00 |
| Hmw PQ-1, ppm | 3.00 | 3.00 | 3.00 | 3.00 | 3.00 | 3.00 |
| Tetronic 904 | 0.1 | 0.1 | 0.1 | 0.1 | 0.1 | 0.1 |
| EDTA | 0.1 | 0.1 | 0.1 | 0.1 | 0.1 | 0.1 |
| NaCl | 0.22 | 0.22 | 0.22 | 0.22 | 0.22 | 0.22 |
| Boric acid | 0.6 | 0.6 | 0.6 | 0.6 | 0.6 | 0.6 |
| Sodium borate 10H2O | 0.182 | 0.182 | 0.182 | 0.182 | 0.182 | 0.182 |
| Trisodium citrate 2H2O | 0.65 | 0.65 | 0.65 | 0.65 | 0.65 | 0.65 |
| HPMC, % | 0.039 | 0.039 | 0.039 | 0.039 | 0.039 | 0.039 |
| *C. albicans* 10231 6 hr log kill | 1.6 | 2 | 3.2 | 0.1 | 0 | 0.1 |

TABLE IX-continued

| Ingredients | DT1110-44-10 | DT1110-44-11 | DT1110-44-12 | DT1110-44-13 | DT1110-44-14 | DT1110-44-15 |
|---|---|---|---|---|---|---|
| sum, alex only + CXG only | | 1.6 | 1.7 | | | |
| Candida log kill synergy ratio | | 1.25 | 1.88 | | | |

This example demonstrates in solutions 44-2 and 44-3, representing compositions of the present invention, that synergistic activity against *C. albicans* does not require the presence of a surfactant. This example also demonstrates that the concentrations of the chlorhexidine and the surfactant may impact the resulting synergy, with increasing synergy at 3.00 ppm chlorhexidine with increasing surfactant concentration, and decreasing synergy at 1.00 ppm chlorhexidine with increasing surfactant concentration. This same relationship was observed for Pluronic F87 in examples 2 and 3.

Example 5

In this example, solutions shown in Tables X and XI below were prepared and tested according to the methods described above. In this example, several different Tetronic and Pluronic surfactants at 0.10%, along with 0.039% HPMC were used. This example does not employ a design using a rigorous mathematical test of synergy, as the intent was to show that a combination of alexidine and chlorhexidine functions the same with a variety of surfactants. Moreover, solution 64-5 is a repeat of solution 54-4, and demonstrated similar log kill (4.0 vs 3.4 log, respectively).

TABLE X

| Ingredients | DT1110-64-1 | DT1110-64-2 | DT1110-64-3 | DT1110-64-4 |
|---|---|---|---|---|
| Alexidine 2HCl, ppm | 1.05 | 1.05 | 1.05 | 1.05 |
| Chlorhexidine digluconate, ppm | 3.00 | 3.00 | 3.00 | 3.00 |
| Hmw PQ-1, ppm | 3.00 | 3.00 | 3.00 | 3.00 |
| EDTA | 0.10 | 0.10 | 0.10 | 0.10 |
| NaCl | 0.22 | 0.22 | 0.22 | 0.22 |
| Boric acid | 0.60 | 0.60 | 0.60 | 0.60 |
| Sodium borate 10H2O | 0.182 | 0.182 | 0.182 | 0.182 |
| Trisodium citrate 2H2O | 0.65 | 0.65 | 0.65 | 0.65 |
| HPMC | 0.039 | 0.039 | 0.039 | 0.039 |
| Tetronic 304 | 0.10 | | | |
| Tetronic 904 | | 0.10 | | |
| Tetronic 1107 | | | 0.10 | |
| Tetronic 1307 | | | | 0.10 |
| Pluronic F87 | | | | |
| Pluronic F127 | | | | |
| Pluronic F68 | | | | |
| *C. albicans* 10231 6 hr log kill | 3.5 | 4.8 | 4.8 | 3.9 |

TABLE XI

| Ingredients | DT1110-64-5 | DT1110-64-6 | DT1110-64-7 |
|---|---|---|---|
| Alexidine 2HCl, ppm | 1.05 | 1.05 | 1.05 |
| Chlorhexidine digluconate, ppm | 3.00 | 3.00 | 3.00 |
| Hmw PQ-1, ppm | 3.00 | 3.00 | 3.00 |
| EDTA | 0.10 | 0.10 | 0.10 |
| NaCl | 0.22 | 0.22 | 0.22 |
| Boric acid | 0.60 | 0.60 | 0.60 |
| Sodium borate 10H2O | 0.182 | 0.182 | 0.182 |
| Trisodium citrate 2H2O | 0.65 | 0.65 | 0.65 |
| HPMC | 0.039 | 0.039 | 0.039 |
| Tetronic 304 | | | |
| Tetronic 904 | | | |
| Tetronic 1107 | | | |
| Tetronic 1307 | | | |
| Pluronic F87 | 0.10 | | |
| Pluronic F127 | | 0.10 | |
| Pluronic F68 | | | 0.10 |
| *C. albicans* 10231 6 hr log kill | 4 | 4.3 | 3.3 |

Example 6

In this example, solutions shown in Tables XII and XIII below were prepared and tested according to the methods described above. The solutions in Table XII include varying concentrations of chlorhexidine in the range of about 2.00 ppm to about 5.00 ppm, while maintaining the concentration of alexidine at 1.05 ppm. The solutions in Table XIII include varying concentrations of chlorhexidine in the range of about 2.00 ppm to about 5.00 ppm, while maintaining the concentration of alexidine at 0.80 ppm.

TABLE XII

| Components | DT1200-98-1 | DT1200-X98-2 | DT1200-98-3 | DT1200-98-4 |
|---|---|---|---|---|
| Alexidine 2HCl, ppm | 1.05 | 1.05 | 1.05 | 1.05 |
| Chlorhexidine digluconate, ppm | 5.00 | 4.00 | 3.00 | 2.00 |
| Hmw PQ-1, ppm | 3.00 | 3.01 | 3.01 | 3.01 |
| EDTA | 0.10 | 0.10 | 0.10 | 0.10 |
| NaCl | 0.25 | 0.25 | 0.25 | 0.25 |
| Boric acid | 0.60 | 0.60 | 0.60 | 0.60 |
| Sodium borate 10H2O | 0.182 | 0.182 | 0.182 | 0.182 |
| Trisodium citrate 2H2O | 0.65 | 0.65 | 0.65 | 0.65 |
| Tetronic ® 904 | 0.10 | 0.10 | 0.10 | 0.10 |

TABLE XIII

| Components | DT1200-98-5 | DT1200-98-6 | DT1200-98-7 | DT1200-98-8 |
|---|---|---|---|---|
| Alexidine 2HCl, ppm | 0.80 | 0.80 | 0.80 | 0.80 |
| Chlorhexidine digluconate, ppm | 5.00 | 4.00 | 3.00 | 2.00 |
| Hmw PQ-1, ppm | 3.00 | 3.01 | 3.00 | 3.00 |
| EDTA | 0.10 | 0.10 | 0.10 | 0.10 |
| NaCl | 0.25 | 0.25 | 0.25 | 0.25 |
| Boric acid | 0.60 | 0.60 | 0.60 | 0.60 |
| Sodium borate 10H20 | 0.182 | 0.182 | 0.182 | 0.182 |
| Trisodium citrate 2H20 | 0.65 | 0.65 | 0.65 | 0.65 |
| Tetronic ® 904 | 0.10 | 0.10 | 0.10 | 0.10 |

As shown below in Table XIV, all of the solutions in Tables XII and XIII again unexpectedly provide log kills of *C. albicans* of 2.4 and greater. This is consistent with previous results, since the DT1200-98-1 solution containing the highest concentrations of alexidine, 1.05 ppm, and chlorhexidine, 5.00 ppm, produced a log kill of 4.1 and otherwise would have been expected to produce at most a log kill at 6 hours of 1.4+0.5=1.9 log from the simple sum of log kill from alexidine alone in the same formula (about 1.4) and chlorhexidine alone in the same formula (about 0.5). Solution 98-8, containing only 0.80 ppm alexidine along with 2.00 ppm chlorhexidine, showed a 2.4 log kill. This solution, without a synergistic effect, would be expected from the data presented in FIGS. 1 and 2 to produce a log kill of about 1.1 log. Thus, this solution shows a kill enhancement of about 2.4−1.1=1.3 log.

TABLE XIV

| 6 hour $\log_{10}$ reduction | DT1200-98-1 | DT1200-98-2 | DT1200-98-3 | DT1200-98-4 | DT1200-98-5 | DT1200-98-6 | DT1200-98-7 | DT1200-98-8 |
|---|---|---|---|---|---|---|---|---|
| *C. albicans* | 4.1 | 4 | 4.3 | 3.4 | 3.4 | 3.5 | 3.1 | 2.4 |

Example 7

In this example, solutions shown in Table XV below were prepared and tested according to the methods described above. The results demonstrate synergistic activity against *C. albicans* for solution 20-1, representing a composition of the present invention.

TABLE XV

| Ingredients | DT1200-20-1 | DT1200-20-2 | DT1200-20-3 |
|---|---|---|---|
| Alexidine 2HCl, ppm | 0.70 | 0 | 0.70 |
| Chlorhexidine Digluconate, ppm | 1.50 | 1.50 | 0 |
| Hmw PQ-1, ppm | 1.51 | 1.50 | 1.50 |
| EDTA | 0.10 | 0.10 | 0.10 |
| NaCl | 0.22 | 0.22 | 0.22 |
| Boric acid | 0.60 | 0.60 | 0.60 |
| Sodium borate 10H20 | 0.182 | 0.182 | 0.182 |
| Trisodium citrate 2H20 | 0.65 | 0.65 | 0.65 |
| Tetronic 904 | 0.10 | 0.10 | 0.10 |
| *C. albicans* 6 hr log kill | 1.20 | 0.30 | 0.80 |

Thus, by reducing a concentration of alexidine and combining the alexidine with an unexpectedly low concentration of chlorhexidine, a composition is formed that demonstrates synergistic antimicrobial activity against *C. albicans*. Although one or more additional antimicrobial components, for example, Polyquaternium-1, may be included in a composition including both alexidine and chlorhexidine, the presence of the additional antimicrobial component is not necessary. Rather, by employing the combination of each of alexidine and chlorhexidine at relatively low concentrations, a synergistic effect occurs allowing for the increased log kill of *C. albicans* to thereby result in the reduction of the likelihood of incidence of corneal staining and/or infiltrates. As a result, lens wearers using multipurpose lens care solutions including the above described compositions may experience increased comfort and decreased likelihood of infection, infiltrates, redness of the eye, and/or eye disease.

Unless otherwise indicated, all numbers expressing quantities of ingredients, properties such as molecular weight and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are individually incorporated herein by reference in their entirety.

It is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. An ophthalmic composition comprising:
   from 0.8 ppm to 1.05 ppm alexidine;
   from 2 ppm to 5 ppm chlorhexidine; and
   from about 0.5 ppm to about 3.3 ppm poly[(dimethyliminio)-2-butene-1,4-diyl chloride], α-[4-[tris(2-hydroxyethyl)ammonio]-2-butenyl]-Ω-[tris(2-hydroxyethyl)ammonio]-dichloride,
   wherein the composition exhibits synergistic antimicrobial activity against *Candida albicans* by reducing a concentration of *Candida albicans* by at least 2.4 log.

2. The ophthalmic composition of claim 1, further comprising a chelating agent.

3. The ophthalmic composition of claim 2, wherein the chelating agent is ethylenediaminetetraacetic acid (EDTA).

4. The ophthalmic composition of claim 1, wherein EDTA is present at a concentration of from about 0.05% to about 1% by weight per volume.

5. The ophthalmic composition of claim 1, further comprising a surfactant.

6. The ophthalmic composition of claim 1, further comprising a buffer agent.

7. The ophthalmic composition of claim 6, wherein the buffer agent is a boric acid and borate buffering system.

8. The ophthalmic composition of claim 1, further comprising a tonicity component.

9. The ophthalmic composition of claim 8, wherein the tonicity component is sodium chloride.

10. The ophthalmic composition of claim 1, further comprising sodium citrate.

11. The ophthalmic composition of claim 1, further comprising a viscosity-inducing component.

12. The ophthalmic composition of claim 1, further comprising from about 0.05% to about 0.25% by weight per volume hydroxypropyl methylcellulose.

13. The ophthalmic composition of claim 1, further comprising from about 0.039% to about 0.15% by weight per volume hydroxypropyl methylcellulose.

14. An ophthalmic composition comprising:
   from 0.8 ppm to 1.05 ppm alexidine;
   from 2 ppm to 5 ppm chlorhexidine;
   from about 0.5 ppm to about 3.3 ppm poly[(dimethyliminio)-2-butene-1,4-diyl chloride], α-[4-[tris(2-hydroxyethyl)ammonio]-2-butenyl]-Ω-[tris(2-hydroxyethyl)ammonio]-dichloride;
   from about 0.04 to about 0.15% by weight per volume of ethylenediaminetetraacetic acid (EDTA);
   from about 0.18 to about 0.70% by weight per volume of sodium chloride;
   from about 0.50 to about 0.66% by weight per volume of boric acid;
   from about 0.15 to about 0.30% by weight per volume of sodium borate;
   from about 0.22 to about 0.80% by weight per volume of sodium citrate;
   from about 0.03 to about 0.15% by weight per volume of a surfactant; and
   from about 0.03 to about 0.25% by weight per volume of a viscosity-inducing component,
   wherein alexidine and chlorhexidine together exhibit synergistic antimicrobial activity against *Candida albicans* by reducing a concentration of *Candida albicans* by 2.4 to 4.0 log.

15. A method of disinfecting a contact lens comprising: contacting the contact lens with a disinfecting solution, the disinfecting solution including the ophthalmic composition of claim 1; and removing the contact lens from the disinfecting solution.

16. The method of claim 15, wherein the contacting step includes contacting the contact lens with the disinfection solution for at least six hours.

17. The method of claim 15, wherein the disinfection solution further includes from about 0.05% to about 1% weight per volume ethylenediaminetetraacetic acid (EDTA).

18. The ophthalmic composition of claim 1, comprising 0.8 ppm alexidine.

19. The ophthalmic composition of claim 1, comprising 1.05 ppm alexidine.

* * * * *